United States Patent [19]

Yoshida et al.

[11] Patent Number: 5,081,032

[45] Date of Patent: Jan. 14, 1992

[54] ANTI-HUMAN PULMONARY ADENOCARCINOMA MONOCLONAL ANTIBODY

[75] Inventors: Hajime Yoshida, Kanagawa; Kenya Shitara, Tokyo, both of Japan

[73] Assignee: Kyowa Hakko Kogyo Co., Ltd., Tokyo, Japan

[21] Appl. No.: 371,808

[22] Filed: Jun. 27, 1989

[30] Foreign Application Priority Data

Jun. 30, 1988 [JP] Japan .................. 63-163433
Jun. 30, 1988 [JP] Japan .................. 63-163434

[51] Int. Cl.$^5$ .................. C12N 5/20; C12N 15/02; C07K 15/28; C12P 21/08
[52] U.S. Cl. .................. 435/240.27; 530/387; 424/85.8; 435/172.2; 435/70.21
[58] Field of Search .................. 530/387; 435/240.27, 435/172.2, 70.21; 424/85.8

[56] References Cited

FOREIGN PATENT DOCUMENTS 0118365 9/1984 European Pat. Off. .
0155172 9/1985 European Pat. Off. .
0242727 10/1987 European Pat. Off. .
0252769 1/1988 European Pat. Off. .
0285143 10/1988 European Pat. Off. .

OTHER PUBLICATIONS

Hellstrom et al., Cancer Res. 46:3917–23, 1986.
Mazauric et al., Cancer Res. 42:150, 1982.
Radosevich et al., Cancer Res. 45:5808, 1985.
Hanai et al., Cancer Res. 46:4438, 1986.
Kipps et al., pp. 108-1–108.9 in Weir et al. Eds., Handbook of Exptl. Immunol., vol. 1, Blackwell Sci. Publ., 1986.
Campbell, Monoclonal Antibody Technology, Elsevier Press, 1984, 265 pages.
Johnston et al., Cancer Res. 46:6462, 1986.

*Primary Examiner*—Esther L. Kepplinger
*Assistant Examiner*—Paula Hutzell
*Attorney, Agent, or Firm*—Nixon & Vanderhye

[57] ABSTRACT

Anti-human pulmonary adenocarcinoma monoclonal antibody ALC-864 which belongs to the class IgG$_1$, reacts with human pulmonary adenocarcinoma cells but not with normal human cells, recognizes proteins as antigens, and is useful for the identification of pulmonary adenocarcinoma selectively from among normal cells and for distinguishing this cancer from among other types of cancer.

2 Claims, 3 Drawing Sheets

ANTI-HUMAN PULMONARY ADENOCARCINOMA MONOCLONAL ANTIBODY

FIELD OF THE INVENTION

This invention relates to a monoclonal antibody characterized by its reactivity to human pulmonary adenocarcinoma, its ability to recognize antigens which are proteins, and to a pathologic or serologic diagnostic method for monitoring pulmonary adenocarcinoma using the same.

BACKGROUND OF THE INVENTION

Methods of producing tumor-specific monoclonal antibodies which comprise cultivating hybridomas obtained by fusion of antibody-producing cells derived from immunized animals with myeloma cells have been reported recently. Methods of producing monoclonal antibodies to human pulmonary cancer by such techniques have also been reported [Cancer Res., 42, 150 (1982); Cancer Res., 42, 3187 (1982); J. Surgical Res., 30, 403 (1981); Transplantation Proceed., XIII (4), 1942 (1981); J. Immunol., 131 (1), 497 (1983); Seishi Kyoizumi: Abstracts of Papers Presented at the 1983 Meeting of the Japanese Society for Immunology, page 212 (Abstract No. 107) (1983)].

However, most of those monoclonal antibodies react with cancer species other than pulmonary cancer and in many cases also with normal human cells. Those which can be said to be specific to pulmonary cancer are very few in number.

Recently reported are methods of a serodiagnosis of pulmonary adenocarcinoma using monoclonal antibodies which recognize sialylated glycoproteins or glycolipids as antigens [Cancer Res., 47, 1267-1272 (1987); International Journal of Cancer, 36, 421-425 (1985), Cancer Res., 45, 3711-3717 (1985); JP-A-62-80558 (the term "JP-A" as used herein means "an unexamined published Japanese patent application")]. In all of these reports there is no mention of serodiagnosis of pulmonary adenocarcinoma with a monoclonal antibody recognizing proteins as antigens.

The anti-human pulmonary squamous cell carcinoma monoclonal antibody SLC-454 (hereinafter briefly referred to as SLC-454) is a monoclonal antibody isolated by the present inventors. In a serodiagnostic system which uses this antibody, the percentage of positive reactions among pulmonary adenocarcinoma cases is 25%; see EP-A-0252769 or U.S. Pat. No. 4,892,935.

Serodiagnostic systems for pulmonary adenocarcinoma which use SLC-454, are already of great clinical importance. However, the reactivity of SLC-454 to pulmonary adenocarcinoma is not sufficiently high so that it often gives a high incidence of false-positive reactions with benign pulmonary diseases.

A monoclonal antibody reacting specifically with pulmonary adenocarcinoma, if available, would be useful in the diagnosis and treatment of pulmonary adenocarcinoma. While some monoclonal antibodies to pulmonary adenocarcinoma are known, the advent of better antibodies is waited for.

SUMMARY OF THE INVENTION

An object of the present invention is to provide a monoclonal antibody useful in pathologic or serologic diagnosis and/or monitoring of pulmonary adenocarcinoma.

The present inventors found that a monoclonal antibody produced by hybridomas derived, by cell fusion, from spleen cells of an antibody-producing mouse immunized with a high-molecular fraction of the pleural exudate of a human pulmonary adenocarcinoma patient and mouse myeloma cells has good reactivity to pulmonary adenocarcinoma and is useful in the serodiagnosis, pathologic diagnosis and treatment of pulmonary adenocarcinoma.

The present inventors further found that a sandwich-technique enzyme immunoassay comprising using the above-mentioned monoclonal antibody as the first antibody and the anti-human pulmonary squamous cell carcinoma monoclonal antibody SLC-454 labeled with an enzyme or a radioisotope as the second antibody provides a highly accurate and reliable serodiagnosis which gives a high percentage of positive reactions with pulmonary adenocarcinoma.

DETAILED DESCRIPTION OF THE INVENTION

In one aspect, the invention provides an anti-human pulmonary adenocarcinoma monoclonal antibody obtained by producing hybridomas by cell fusion of spleen cells of a mouse immunized with a high-molecular weight fraction of the pleural exudate of a human pulmonary adenocarcinoma patient and mouse myeloma cells, selecting a monoclonal antibody having specificity to human pulmonary adenocarcinoma, cultivating the corresponding hybridoma cell line in a medium or administering the same to mice to thereby cause accumulation of the ascitic fluid in said mice and recovering said monoclonal antibody from the culture or ascitic fluid.

The monoclonal antibody according to the invention belongs to the class $IgG_1$, reacts with pulmonary adenocarcinoma cells but not with normal human cells and recognizes proteins as antigens.

As a typical example of the monoclonal antibody according to the invention, there may be mentioned ALC-864, which is produced by the hybridoma cell line ALC-864 (deposited at the Fermentation Research Institute, Agency of Industrial Science and Technology of Japan 1-3, Higashi 1-chome, Tsukuba-shi, Ibaraki 305, Japan as of Mar. 9, 1988 under the deposit number FERM BP-1783 in accordance with the Budapest Treaty).

In the following, a process for producing the monoclonal antibody according to the invention is described in detail.

(1) Immunization of animal and preparation of antibody-producing cells

Mice 3-10 weeks of age, preferably 8-week-old mice, are immunized with a high-molecular weight fraction of the pleural exudate of a human pulmonary adenocarcinoma patient to prepare antibody-producing cells in the spleen, lymph nodes and peripheral blood of the animals. Mice that have immunological tolerance as a result of pretreatment with normal human lung cells should preferably be used as the mice to be immunized. The immunization is performed generally by administering a high-molecular weight fraction of the pleural exudate of a human pulmonary adenocarcinoma patient (10-500 μg /animal) derived together with an appropriate adjuvant (e.g. complete Freund's adjuvant, or aluminum hydroxide gel plus pertussis vaccine) to the animals subcutaneously, intravenously or intraperitoneally. Thereafter, antigen administration is repeated 2-5 times at 1- to 2-week intervals. Three to seven days after each immunization, the blood is sampled from the eyeground venous plexus and the serum of each sample is tested as to whether it reacts with human pulmonary adenocarcinoma by the enzyme immunoassay technique described below [Enzyme-linked Immunosorbent Assay (ELISA), published by Igaku Shoin, Tokyo, 1976], for instance.

Enzyme immunoassay technique:

The membrane components of normal or tumor cells or tissues (membrane fragment fraction containing 10-1000 μg of proteins per milliliter) are destributed into wells of a 96-well plate for EIA (Flow Laboratories) (100-200 μl per well). After standing at 4° C. for 15 to 40 hours, each well is deprived of the supernatant and, then, washed well with deionized water or phosphate-buffered saline (PBS; 1.83 g of disodium phosphate, 0.21 g of monopotassium phosphate and 7.65 g of sodium chloride in 1 liter of distilled water, pH 7.2). Then, 1% BSA (bovine serum albumin)-containing PBS solution (BSA-PBS) is distributed into the wells (100-200 μl per well) and protein binding residues remaining on the plate are blocked by standing at 4° C. for 15 to 40 hours. After discarding the BSA-PBS, the wells are washed well with deionized water or PBS. Samples (mouse sera, hybridoma culture supernatants, or purified monoclonal antibodies; each as the first antibody) are diluted with BSA-PBS and the dilutions are distributed into the wells (100 μl per well), followed by standing at 4° C. for 15 hours. After washing the wells with one portion of deionized water and then with 6 portions of 2 M NaCl solution, a 100-fold dilution of a rabbit anti-mouse immunoglobulin IgG-peroxidase conjugate (produced by DAKO and distributed by Kyowa Medex; used as the second antibody) is distributed into the wells (100 μl per well). The plate is then allowed to stand at room temperature for 2 hours.

After washing the wells thoroughly with PBS, an ABTS substrate solution [prepared by dissolving 550 mg of 2,2'-azinobis(3-ethylbenzothiazoline-6-sulfonic acid) diammonium salt in 1 liter of 0.1 M citrate buffer (pH 4.2) and adding, just prior to use, hydrogen peroxide to a concentration of 1 μl/ml] is applied and the color development is determined by measuring the absorbance at 415 nm ($OD_{415}$ nm). Those mice that strongly react with the pulmonary adenocareinoma cells, tissues, membrane components thereof or high-molecular weight fractions of the pleural exudate of human pulmonary adenocarcinoma patients are used as human pulmonary adenocarcinoma-immunized mice, namely as sources of supply of antibody-producing cells for hybridoma production.

When cells per se are used as the antigen in performing an enzyme immunoassay, the target cells are cultured on a Falcon 3072 plate, 0.25% glutaraldehyde-PBS is added and, after allowing it to stand at room temperature for 1-2 hours, the plate is washed well with PBS. Then, 100-200 μl of 1% BSA-PBS is added and, after 2 hours of standing, the plate is washed well with deionized water or PBS and submitted to antibody titer determination, which is conducted in the same manner as the case where an ordinary antigen-coated plate is used.

For submitting to cell fusion, a high-molecular weight fraction of the pleural exudate of a human pulmonary adenocarcinoma patient (10-400 μg/animal) is intraperitoneally administered to mice to be immunized 3-4 days prior to the fusion treatment. The spleen is excised, cut into fragments in Eagle's minimal essential medium (MEM; Nissui Pharmaceutical), loosened up with a pair of forceps, and centrifuged at 1,200 rpm for 5 minutes. The supernatant is discarded, and the cells obtained as the sediment are deprived of erythrocytes by 1- to 2-minute treatment with Tris-ammonium chloride buffer (pH 7.65), washed with three portions of MEM, and used as the spleen cells for fusion.

The high-molecular weight fraction of pleural exudate of a human pulmonary adenocarcinoma patient used as an immunogen is prepared in the following manner.

The pleural exudate of a human pulmonary adenocarcinoma patient stored at $-80°$ C. is thawed, and then, centrifuged at 3,000 rpm for 10 minutes to remove solids. The resulting supernatant is passed through a Cellulofine GCL-2000SF (manufactured by Seikagaku Kogyo) column and high-molecular weight (1,000,000 or more) fractions were collected for use as the high-molecular weight fraction of pleural exudate of a human pulmonary adenocarcinoma patient.

(2) Preparation of myeloma cells

A mouse-derived established myeloma cell line is used. Suitable examples of such cell lines are the 8-azaguanine resistant (BALB/c-derived) mouse myeloma cell lines P3-X63Ag8-U1 (P3-U1) [Current Topics in Microbiology and Immunology-1] [European J. Immunology, 6, 511-519 (1976)], SP2/0-Ag14 (SP-2) [Nature, 276, 269-270 (1978)], P3-X63-Ag8653 (653) [J. Immunology, 123, 1548-1550 (1979)] and P3-X63-Ag8 (X63) [Nature, 256, 495-497 (1975)]. These cell lines are subcultured in 8-azaguanine medium (normal medium prepared by adding, to RPMI-1640 medium, glutamine (1.5 mM), 2-mercaptoethanol ($5\times10^{-5}$ M), gentamicin (10 μg/ml) and fetal calf serum (FCS; produced by CSL) (10%), further supplemented with 8-azaguanine (15 μg/ml)]. The cell line selected for cell fusion should be transferred to normal medium 3-4 days before cell fusion to ensure the cell count of not less than $2\times10^7$ on the day of fusion.

(3) Cell fusion

The antibody-producing cells immunized in (1) and the myeloma cells obtained in (2) are washed well with MEM or PBS and mixed in a cell number ratio of antibody-producing cells: myeloma cells 5 to 10:1 and then centrifuged at 1,200 rpm for 5 minutes. The supernatant is discarded and the cell sediment is loosened up. With stirring at 37° C., a mixture of 2 g of polyethylene glycol 1000 (PEG-1000), 2 ml of MEM and 0.7 ml of dimethyl sulfoxide is added thereto in an amount of 0.2–1 ml per $10^3$ antibody-producing cells and, following several additions of 1–2 ml of MEM at 1- to 2-minute intervals, the whole volume is made to 50 ml by further adding MEM. After centrifugation at 900 rpm for 5 minutes, the supernatant is discarded and the cell sediment is loosened gently. To the cells is added 100 ml of normal medium (RPMI-1640 with 10% FCS). The cells are suspended in the medium by gentle drawing up into and discharging from a measuring pipette.

The suspension obtained is distributed, in 100 μl-portions, into each well of a 96-well incubation plate. Incubation is carried out in a 5% $CO_2$ incubator at 37° C. for 24 hours. HAT medium [normal medium supplemented with hypoxanthine ($10^{-4}$ M), thymidine ($1.5 \times 10^{-5}$ M) and aminopterine ($4 \times 10^{-7}$ M)] is added to the incubation plate (100 μl per well) and incubation is conducted for another 24 hours. Thereafter, the culture supernatant (100 μl) is discarded and the same volume of fresh HAT medium is added instead at 24-hour intervals for 2 days. The incubation in the $CO_2$ incubator at 37° C. is continued for 10–14 days.

For those wells in which fused cells grown and forming colonies are found, the supernatant (100 μ) is discarded and the same volume of HT medium (HAT medium minus aminopterine) is added, followed by medium replacement with fresh portions of HT medium at 24-hour intervals for 2 days.

After 3–4 days of cultivation in HT medium, a portion of the culture supernatant is collected and assayed for antibody titer relative to human pulmonary adenocarcinoma by the above-mentioned enzyme immunoassay method or immunohistological evaluation method (ABC method) ["Koso-Kotai Ho (Enzyme-antibody Method)" published by Gakusai Kikaku, p. 100, (1985)]. Simultaneously, the reactivities to normal human cells or tissues or membrane components thereof, among others, are also determined in the same manner, and those wells for which specific reactivity is found to human pulmonary adenocarcinoma cells or tissues, membrane components thereof or high-molecular weight fractions of the pleural exudate of human pulmonary adenocarcinoma patients are selected. For the wells showing strong reactivity to human pulmonary adenocarcinoma cells or tissues, membrane components thereof or high-molecular weight fractions of the pleural exudate of human pulmonary adenocarcinoma patients, but no reactivity to normal human cells or tissues or membrane components thereof, among others, cloning is repeated twice by the limiting dilution technique. In this way, those clones for which high antibody titer values are stably obtainable relative to human pulmonary adenocarcinoma cells or tissues, membrane components thereof or high-molecular weight fractions of the pleural exudate of human pulmonary adenocarcinoma patients are selected as anti-human pulmonary adenocarcinoma monoclonal antibody-producing hybridoma cell lines.

(4) Preparation of monoclonal antibody

Eight- to ten-week-old female BALB/c mice treated with pristane [intraperitoneally administered with 0.5 ml of 2,6,10,14-tetramethylpentadecane (pristane) and fed for 2-weeks] are intraperitoneally injected with the antihuman pulmonary adenocarcinoma monoclonal antibody-producing hybridomas obtained in (3) at a dose of $2-4 \times 10^6$ cells per animal. In 10–21 days, the hybridomas cause ascites tumor in the mice. The ascitic fluid is collected from such a mouse, centrifuged at 3,000 rpm for 5 minutes to remove solids, subjected to salting out with 50% ammonium sulfate, dialyzed against 0.04 M phosphate buffer (pH 8.0) supplemented with 0.03 M NaCl, and applied to DE52 (Whatman) column (bed volume: 50 ml) at a flow rate of 20 to 30 ml/hr. An IgG fraction is collected and used as a purified monoclonal antibody.

The isotype of the antibody is determined by Ouchterlony's method (double immunodiffusion) [Seibutsukagaku Jikkenho (Methods in Experimental Biochemistry), vol. 15, Introduction to Experimental Immunology, p.74, Gakkai Shuppan Center, 1981].

The protein quantity is estimated by the Folin method, followed by calculation based on the absorbance at 280 nm [1.4 ($OD_{280}$) is approximately equal to 1 mg of immunoglobulin per milliliter].

The monoclonal antibodies thus obtained are evaluated for specificity characteristics based on the reactivities to normal and tumor tissues and membrane components thereof derived from a variety of human organs obtained from a plurality of subjects, the reactivities to a variety of cultured human normal or tumor cell lines or cultured human fetal cell lines or membrane components derived therefrom, the reactivity to the hitherto known carcinoembryonic antigen (CEA), and the reactivity to serum from healthy persons and patients as determined by the enzyme immunoassay method, fluorescent antibody method, immunohistological evaluation method (ABC method), etc.

The thus-obtained monoclonal antibody which reacts specifically with human pulmonary adenocarcinoma is expected to be useful in the diagnosis of pulmonary cancer, which is to be performed in the manner of serodiagnosis, histologic diagnosis or imaging, among others, and further in the treatment of pulmonary cancer which comprises administering to pulmonary cancer patients said antibody either as such or in the form of the so-called immunotoxin, namely a form of the antibody bound to an anticancer agent or a toxin. It is also expected that by an affinity column chromatography in which this tumor-specific monoclonal antibody is used, the antigen reactive with the monoclonal antibody is collected and purified, and then the purified antigen is used in development of a pulmonary cancer vaccine.

(5) Serodiagnosis of pulmonary cancer

The serodiagnosis by the enzyme immunoassay method is performed as follows:

A first antibody preparation (10–100 μg/ml) is distributed into the wells of a 96-well plate for EIA (50–200 μl per well). The plate is allowed to stand at 4° C. for 15 to 40 hours or at room temperature for 2 to 4 hours. After washing with PBS, 200 μl of 1% BSA-PBS is added to each well, followed by further standing at 4° C. for 15 hours or at room temperature for 2 hours. The plate is then washed well with PBS, and 50–100 μl of a 1-to 100-fold dilution of a serum sample is added to each well. After allowing it to stand at 4° C. for 15 hours or at room temperature for 2 hours, the plate is washed well with PBS. Then, a biotinylated or peroxidase-labeled second antibody (10–100 μg/μl) is added to the wells (50–100 μl per well) and the plate is further allowed to stand at 4° C. for 15 hours or at room temperature for 2 to 4 hours. When a biotinylated antibody is used as the second antibody, the plate is washed well with PBS, avidin-biotin-peroxidase (10 μg/ml) is added to the wells (50–100 μl per well), and the plate is allowed to stand at room temperature for 30 minutes and then washed well with PBS. Then, an ABTS substrate solution is added, as the substrate solution, in an amount of 50-100 μl per well. After allowing the plate to stand at room temperature for 10-30 minutes, the reaction is terminated by adding 5% SDS (sodium dodecyl sulfate) solution in an amount of 50-100 μl per well. The $OD_{415nm}$ value is measured for each well and the antigen quantity in the serum sample is calculated based on the intensity of the color developed. By comparing the antigen levels in the sera of healthy subjects with those in the sera of patients with lung cancer, a normal level range is defined. When the level in question exceeds such a range, the test is regarded as positive.

The serodiagnosis by the radioimmunoassay method can be carried out in accordance with the method described in Cancer Res. 45, 435 (1985).

The serodiagnostic method described above can be used also in evaluating the effects of cancer therapy employed or for predicting the recurrence of cancer by measuring at appropriate time intervals (i.e. monitoring) the serum cancer antigen level in a patient.

(6) Antigen analysis

When in performing the enzyme-linked immunoassay, immunohistochemical staining, or serodiagnostic method, the antigens (pulmonary adenocarcinoma cell membrane components, cultured lung cancer cell lines, lung cancer tissues) are pretreated with reagents such as enzymes (e.g., neuraminidase, protease) or periodic acid and then reacted with the monoclonal antibodies, the subsequent comparison for differences in reactivity to the monoclonal antibodies between the original antigens without such pretreatment and the antigens pretreated in the above manner can shed light on the chemical characteristics of the antigens, that is the chemical characteristics of the antigenic sites which the monoclonal antibodies recognize. Thus, if the antigenicity disappears upon treatment with neuraminidase, it is estimated that sialic acids are associated with the antigenic determinants. If the antigenicity disappears upon protease treatment, the involvement of proteins in the antigenic determinants is probable. If the antigenicity disappears upon periodic acid treatment, sugar chains are presumably associated with the antigenic determinants.

The pathologic diagnosis using the monoclonal antibody according to the invention is performed by the immunohistochemical staining method (the ABC method).

A method of determining the presence of the pulmonary adenocarcinoma antigen by a sandwich enzyme immunoassay comprising using a ALC-864 as the first antibody and SLC-454 as the second antibody are described in detail below.

Monoclonal antibody SLC-454 is disclosed in EP-A-0252769 or U.S. patent Ser. No. 070,052 (the disclosure of which is hereby incorporated by reference), the inventors being the same as in the instant application, and can be produced as described in these documents using the hybridoma cell line SLC-454 which can produce this monoclonal antibody. Hybridoma cell line SLC-454 has been deposited at the European Collection of Animal Cell Culture (Great Britain) under the deposit number 86070306 under the Budapest Treaty.

The serodiagnostic method is performed in accordance with the above-described enzyme immunoassay.

Enzyme-labeling of the monoclonal antibody SLC-454 is performed using peroxidase, urease, alkaline phosphatase and β-galactosidase, as the enzyme, for instance by the periodic acid-aided crosslinking method [J. Histochem. Cytochem., 22, 1084-1091 (1971)].

The periodic acid-aided crosslinking with peroxidase is carried out, for example, as follows.

Peroxidase is dissolved in 1 ml of 0.3 M sodium bicarbonate buffer (pH 8.1), 0.1 ml of a 1% solution of fluoro-2,4-dinitrobenzene in ethanol and, to the mixture, 1 ml of 0.06 M periodic acid is added, and the reaction is allowed to proceed at room temperature for 30 minutes. The reaction mixture is dialyzed against 0.01 M carbonate buffer (pH 9.5) to give a dialyzate containing peroxidase having dinitrophenyl (DNP)-modified amino groups and aldehyde group-introduced sugar moieties. The antibody (5 mg of protein) is added to the dialyzate, the reaction is allowed to proceed at room temperature for 2 hours, the reaction mixture is dialyzed against 0.01 M phosphate buffer (pH 7.2), and the dialyzate is subjected to Sephadex G100 column chromatography for gel filtration. An active fraction recovered is used as the enzyme-labeled antibody.

In the case of using peroxidase, an ABTS substrate solution is used and the color development is determined by measuring the absorbance at 415 nm ($OD_{415}$ nm). For urease, a solution containing 8 mg of bromocresol purple, 100 mg of urea and 0.2 mM EDTA per 100 ml thereof and having a pH of 4.8 is used as the substrate and the measurement is performed by the method described in J. Immunol. Methods, 53, 187-194 (1982). For alkaline phosphatase, a solution of 1 mg/ml of p-nitrophenyl phosphate in 0.1 M diethanol-amine buffer is used as the substrate.

The enzyme labeling can also be effected through biotin-avidin binding. Labeling with biotin can be conducted by the method described in J. Histochem. Cytochem., 27, 1131-1139 (1979).

Similarly, the pulmonary adenocarcinoma antigen can be determined in the same manner as described above except that SLC-454 is used as the first antibody and biotinylated ALC-864 is used as the second antibody.

According to the present invention, a simplified and efficient serodiagnosis of human pulmonary adenocarcinoma can be effected.

The following examples are presented to illustrate the invention in further detail, but are not intended to be construed to limit the scope of the invention.

EXAMPLE 1

(1) Preparation of immunogen

A high-molecular weight fraction of pleural exudate of a human pulmonary adenocarcinoma patient for use as an immunogen was prepared as follows.

The pleural exudate from a human pulmonary adenocarcinoma patient stored at −80° C. was thawed and centrifuged at 3,000 rpm for 10 minutes to remove solids. The supernatant thus obtained (8 ml) was applied to a Cellulofine GCL-2000SF (Seikagaku Kogyo) column (bed volume : 750 ml) which had been equilibrated with 10 mM phosphate buffer (pH 7.2) containing 0.5 M NaCl to collect a high-molecular weight (1,000,000 or more) fraction (void fraction; fraction Nos. 41-50) for use as the high-molecular weight fraction of the pleural exudate of a human pulmonary adenocarcinoma patient.

Figure 1:
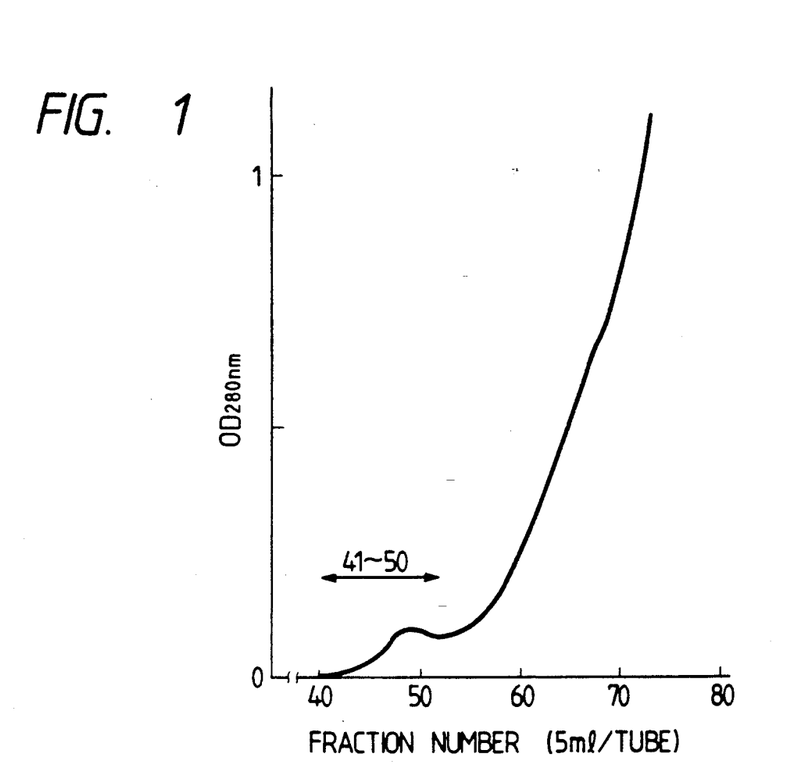
FIG. 1 is a graph showing the pattern of elution of various fractions of a pleural exudate from a Cellulofine GCL-2000SF column.

FIG. 1 shows the elution pattern of the pleural exudate using Cellulofine GCL-2000SF.

(2) Preparation of antibody-producing cells

Normal human lung tissue membrane components were administered intravenously to new-born BALB/c mice within 24 postnatal hours at a dose of 100 μg of protein per animal. After a lapse of 8 weeks, the mice were intraperitoneally administered with the high-molecular weight fraction of the pleural exudate of a human pulmonary adenocarcinoma patient (100 μg of protein per animal) together with aluminum hydroxide gel (2 mg per animal) and killed pertussis vaccine ($1 \times 10^9$ cells per animal), followed by 3-5 immunizations with the same antigen at a dose of 100 μg per animal on the protein basis at 1- to 2-week intervals. From among these immunized mice, those mice whose antisera intensely reacted with human pulmonary adenocarcinoma cells or tissues, membrane fragments derived therefrom or high-molecular weight fractions of the pleural exudate of human pulmonary adenocarcinoma patients were selected as the desired immunized mice, and spleen cells were prepared from such mice and submitted to cell fusion.

(3) Preparation of mouse myeloma cells

The 8-azaguanine-resistant mouse myeloma cell line P3-U1 was cultivated in normal medium to thereby secure not less than $2 \times 10^7$ cells at the time of cell fusion, and submitted to cell fusion as a parent strain.

(4) Hybridoma production

The spleen cells and myeloma cells obtained in (2) and (3), respectively, were used in a ratio of 5:1 and subjected to fusion following the procedure mentioned hereinabove. After cultivation in HAT medium at 37° C. under 5% $CO_2$ for 14 days, fused cells were selected and, after changing the medium to HT medium, cultivation was continued. Based on the results of anti-human pulmonary adenocarcinoma antibody titer determination, active wells were selected and, after changing the medium to normal medium, cloning was repeated twice. Thus was selected the hybridoma cell line ALC-864 capable of producing a monoclonal antibody having no reactivity to any of normal human cells or tissues but having specific reactivity to human pulmonary adenocarcinoma, as determined by enzyme immunoassay or immunohistological evaluation (ABC method).

(5) Monoclonal antibody purification

Pristane-treated 8-week-old female BALB/c mice were intraperitoneally injected with the hybridoma cell line ALC-864 obtained in (4) at a dose of $4 \times 10^6$ cells per animal. In 10-21 days, the hybridoma caused ascites tumors. The ascitic fluid was collected from ascitic fluid-bearing mice (5-10 ml per animal), deprived of solids by centrifugation at 3,000 rpm for 5 minutes, subjected to salting out with 50% ammonium sulfate, dialyzed against 0.04 M phosphate buffer (pH 8.0) supplemented with 0.03 M NaCl, and applied to a DE52 (Whatman) column (bed volume: 50 ml) at a flow rate of 20 to 30 ml/hr. An IgG fraction was collected and used as a purified monoclonal antibody. The isotype of the thus-obtained anti-human pulmonary adenocarcinoma monoclonal antibody was determined by the Ouchterlony method, and it was found to belong to the class $IgG_1$.

(6) Specificity of ALC-864

The results of testing of the anti-human pulmonary adenocarcinoma monoclona antibody ALC-864 for reaction specificity by the ELISA method are summarized below in Table 1.

TABLE 1

| Antigen | Reactivity |
|---|---|
| Tissue | |
| pulmonary squamous cell carcinoma | 3/12 |
| pulmonary adenocarcinoma | 10/12 |
| normal lung | 0/6 |
| normal tissues other than lung | 3/12* |
| Antigen | 0/1 |
| CEA | |
| Cultured cell line | |
| pulmonary squamous cell carcinoma | 3/4 |
| pulmonary adenocarcinoma | 2/5 |
| fetal lung cancer | 0/1 |
| other cancers | 11/21** |
| Normal cells | 0/3 |

Note:
*: weakly reactive with three samples of kidney tissues.
**: reactive with 6 samples of breast cancer cell lines, 3 samples of pancreatic cancer cell lines and 2 samples of uterine cancer cell lines.

EXAMPLE 2

The following immunohistochemical staining of pulmonary adenocarcinoma was performed using the monoclonal antibody ALC-864 obtained in EXAMPLE 1.

Formalin-fixed, paraffin-embedded tissue sections (sliced to a thickness of 5 μm with a microtome) of cancer tissues were each fixed on an egg albumin-coated slide glass, deparaffinized with xylene and rendered hydrophilic stepwise with alcohol-water. Each section was rinsed with deionized water for 5 minutes and then allowed to stand in methanol containing 0.3% $H_2O_2$ at room temperature for 30 minutes for blocking endogenous peroxidases. The section was then washed with PBS for 20 minutes and allowed to stand in diluted normal mouse serum at room temperature for 20 minutes. The excess serum was sucked off from the section, and the section was reacted with the first antibody (anti-human pulmonary adenocarcinoma monoclonal antibody ALC-864, 10 μg/ml) for 30 minutes. After washing, the section was then reacted with a diluted biotinylated antibody (biotinylated rabbit anti-IgG antibody, product of Vector) for 30 minutes, washed further, and reacted with an avidin-biotin-peroxidase complex (Vector) for 30 minutes. After washing, the section was reacted with a peroxidase substrate [0.1% diaminobenzidine tetrahydrochloride prepared by using 0.1 M Tris-hydrochloride buffer (pH 7.2) containing 0.02% $H_2O_2$] for 2 minutes. The reaction was then terminated by cooling in ice. The section was stained with hematoxylin, dehydrated with alcohol-water and xylene, fixed with Canada balsam (product of Merck), and observed under a microscope.

As a result, it was observed that 6 out of 7 samples of the paraffin-embedded sections of pulmonary adenocarcinoma tissues removed from pulmonary adenocarcinoma patients were strongly stained. This suggests that the immunohistochemical staining using the monoclonal antibody ALC-864 can be applied to a pathologic diagnosis of pulmonary adenocarcinoma.

EXAMPLE 3

A suspension of ALC-864 (10 μg/ml) was distributed as a first antibody in 50-μl portions into each well of a 96-well plate for EIA (Flow Laboratories). After standing at 4° C. for 15 hours, the plate was washed with PBS. Then, 1% BSA-PBS was added (200 μl per well). After standing for 15 hours, the plate was washed well with PBS. To the plate were added 4-fold dilutions of normal human-derived sera (44 samples) or of lung cancer patient-derived sera (92 samples) in an amount of 40 μl per well. After standing at 4° C. for 15 hours, the plate was washed well with PBS. Then, biotinylated anti-pulmonary adenocarcinoma monoclonal antibody ALC-864 (10 μg/m%) was added as the second antibody (100 μl per well). The plate was allowed to stand at 4° C. for 15 hours and, then, washed well with PBS. Avidin-biotin-peroxidase complex (10 μg/ml) was distributed in 100μl portions into each well, and the plate was allowed to stand at room temperature for 1 hour and then washed with PBS. Thereafter, the ABTS substrate solution was added in an amount of 100 μl per well and the reaction was allowed to proceed at room temperature for 30 minutes and then terminated by adding 5% SDS solution (100 μl per well). For each well, the color development was determined by measuring the absorbance at 415 nm ($OD_{415nm}$).

Figure 2:
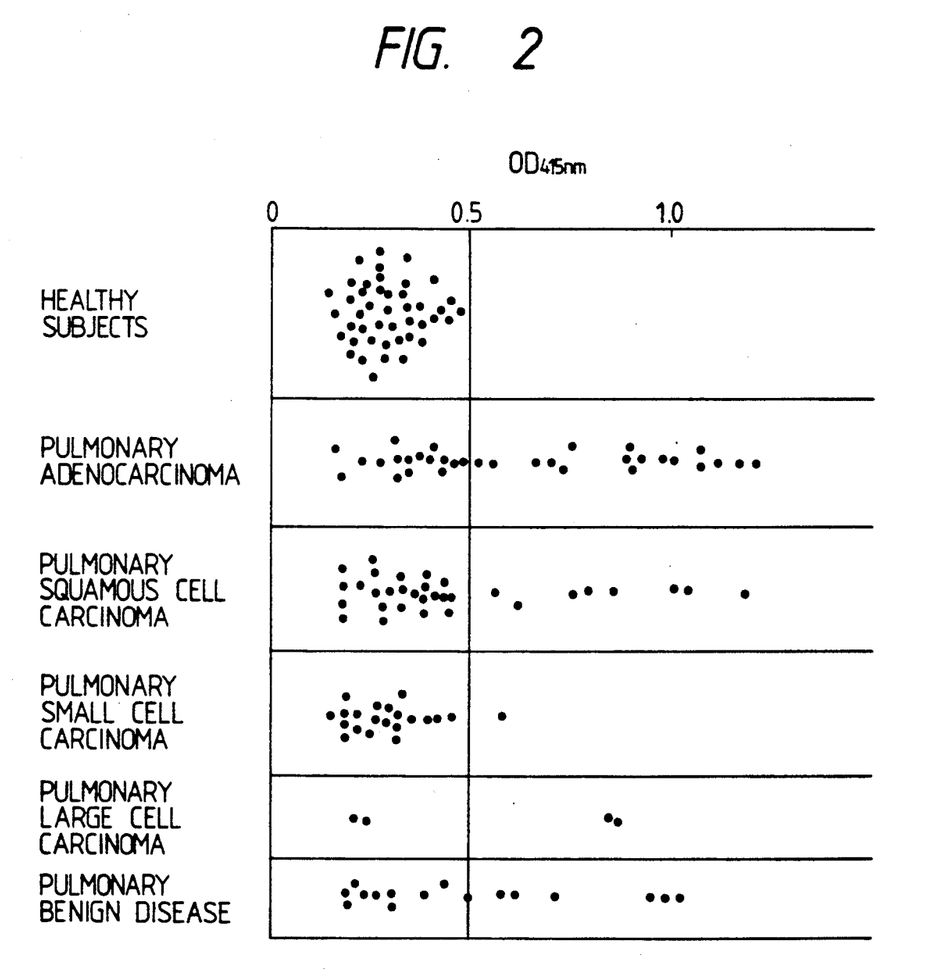
FIG. 2 is a scattergram showing the results of pulmonary cancer serodiagnosis using the monoclonal antibody ALC-864 and distinguishing pulmonary adenocarcinoma from other types of carcinoma.

As shown in FIG. 2, no positive result ($OD_{415nm} > 0.50$) was obtained from among the 44 serum samples from healthy subjects, while 17 out of 33 samples from pulmonary adenocarcinoma patients gave positive results. It is found from these results that the pulmonary adenocarcinoma patients are detectable by serodiagnosis using the monoclonal antibody ALC-864 at a positive rate of 51.5%. Among serum samples of the other cancer patients, the positive results ($OD_{415nm} 0.50$) were obtained in 8 (24%) out of 33 samples of pulmonary squamous cell carcinoma patients, 2 (9.1%) out of 22 samples of pulmonary small cell carcinoma patients, 2 (50%) out of 4 samples of pulmonary large cell carcinoma patients and 6 (37.5%) out of 16 samples of pulmonary benign disease patients.

EXAMPLE 4

For analyzing the antigens which the monoclonal antibody ALC-864 recognizes, pulmonary adenocarcinoma tissue-derived membrane components were treated with the enzymes and reagents described below and then examined for the reactivity with ALC-864.
Enzymes and reagents
  Trypsin (2.5% solution; Gibco)
    0.25% in PBS
  Neuraminidase (Boehringer Mannheim)
    0.1 U/ml in 0.1 M acetate buffer (pH 4.5)-3 mM $CaCl_2$
  α-L-Fucosidase (Boehringer Mannheim)
    0.1 U/ml in 0.1 M phosphate buffer (pH 6.3)
  Protease (Sigma)
    10 U/ml in 0.1 M phosphate buffer (pH 7.2)
  $NaIO_4$ (Wako Pure Chemical Industries)
    50 mM in PBS Thus, the pulmonary adenocarcinoma tissue membrane components (100 μg of proteins per ml) were distributed, in 50-μl portions, into each well of a plate for EIA (Linbro). After standing at 4° C. for 15 hours, the plate was washed three times with PBS. Then, 1% BSA-PBS was distributed into the wells (200 μl per well). The plate was allowed to stand at room temperature for 30 minutes to 2 hours and then washed three times with PBS. One of the above enzyme solutions or reagent solution was distributed into the wells (50 μl per well) and the reaction was carried out at 37° C. for 1 hour. Then, the plate was washed five times with PBS and the monoclonal antibody ALC-864 (10 μg/ml) was distributed into the wells (50 μl per well), followed by allowing it to stand at 4° C. for 15 hours.

After washing five times with Tween-20-PBS (PBS containing 0.05% Tween-20; Tween-20 being a product of Wako Pure Chemical Industries), peroxidase-labeled rabbit anti-mouse IgG (product of DAKO, distributed by Kyowa-Medex: 400-fold dilution) was added (50 per well), and the reaction was carried out at room temperature for 2 hours. The plate was washed five times with Tween-20-PBS, the ABTS substrate solution was added (100 μl), the reaction was conducted for 30 minutes, and the absorbance was measured at 415 nm.

Figure 3:
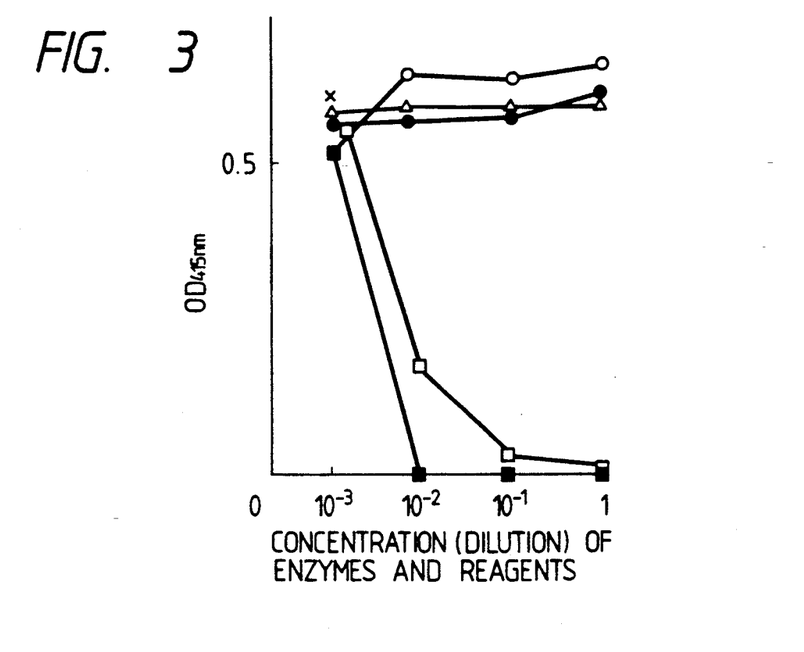
FIG. 3 is a graph showing the changes in reactivity of pulmonary adenocarcinoma tissue-derived membrane components to the monoclonal antibody ALC-864 following treatment with various enzymes and a reagent. The symbol ● stands for treatment with 0.1 U/ml of neuraminidase, △ for treatment with 0.1 U/ml of a-L-fucosidase, □ for treatment with 0.25% trypsin, ■ for treatment with 10 U/ml of protease, ○ for treatment with 50 mM $NaIO_4$, and X for no treatment.

As shown in FIG. 3, the antigenicity completely disappeared upon treatment with trypsin or protease. Based on these results, it was estimated that the monoclonal antibody ALC-864 recognizes proteins.

EXAMPLE 5

A suspension of ALC-864 (10 μg/ml) prepared in Example 1 was distributed as a first antibody in 100-μl portions into each well of a 96-well plate for EIA (Flow Laboratories). After standing at 4° C. for 15 hours, the plate was washed with PBS. Then, 1% BSA-PBS was added (200 μl per well). After standing at 4° C. for 15 hours, the plate was washed well with PBS. To the plate were added 10-fold dilutions of normal human-derived sera (144 samples), lung cancer patient-derived sera (92 samples), gastric cancer patient-derived sera (33 samples), breast cancer patient-derived sera (27 semples), large intestinal cancer patient-derived sera (25 samples), pancreatic cancer patient-derived sera (10 samples), gallbladder or bile duct cancer patient-drived sera (5 samples), pulmonary benign disease patient-derived sera (16 samples), gastric ulcer patient-derived sera (10 samples), hepatic cirrhosis patient-derived sera (3 samples) and pancreatitis patient-derived sera (3 samples) in an amount of 50 μl per well. After standing at 4° C. for 15 hours, the plate was washed well with PBS. Then, biotinylated SLC-454 (10 μg/ml) was added as the second antibody (100 μl per well). The plate was allowed to stand at 4° C. for 15 hours, and then washed well with PBS. Avidin-biotin-peroxidase (10 μg/ml) was distributed in 100-μl portions into each well, and the plate was allowed to stand at room temperature for 1 hour and then washed with PBS. Thereafter, the ABTS substrate solution was added in an amount of 100 μper well and the reaction was allowed to proceed at room temperature for 30 minutes and then terminated by adding 5% SDS solution (100 μl per well). For each well, the color development was determined by measuring the absorbance at 415 nm ($OD_{415nm}$).

Figure 4:
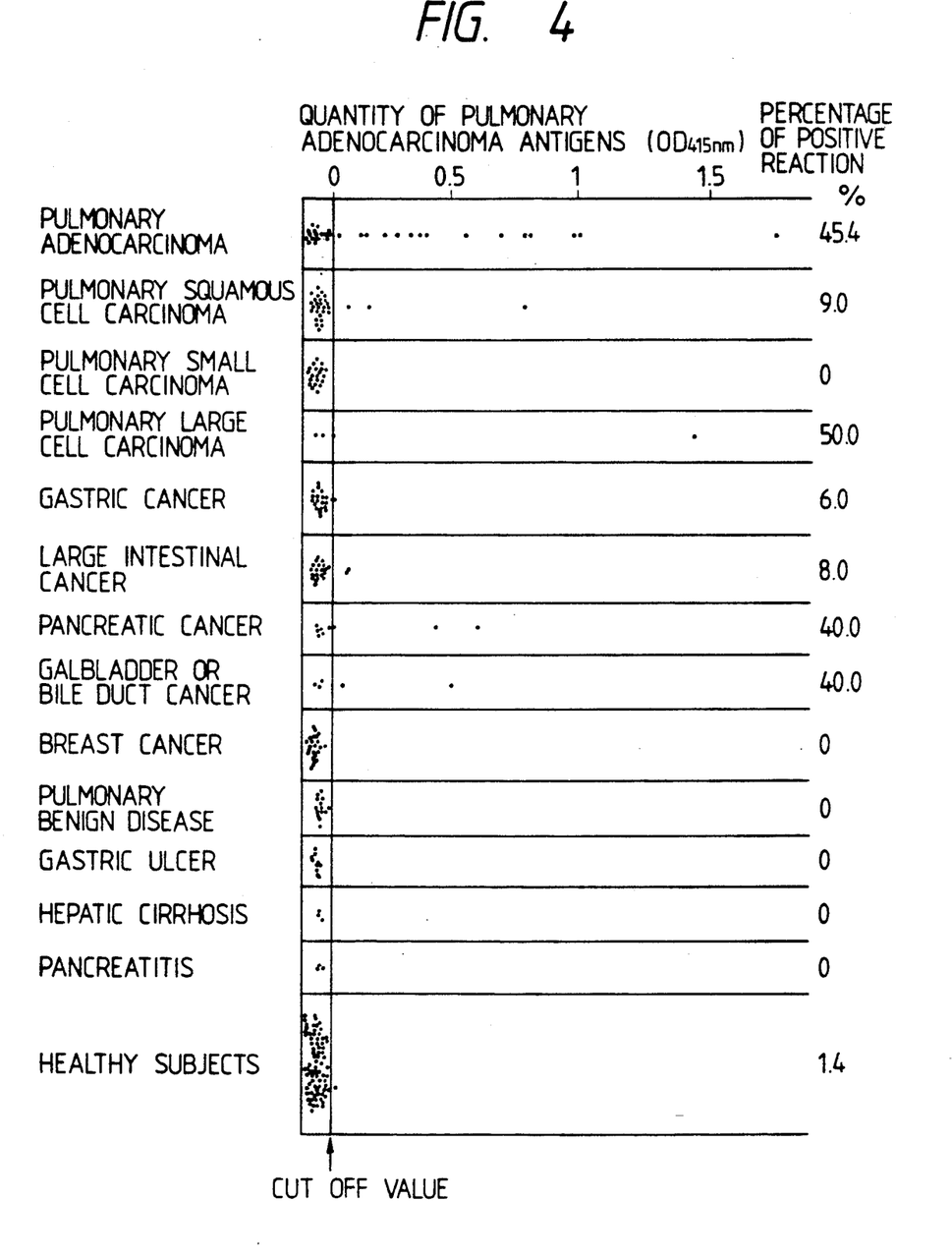
FIG. 4 is a scattergram showing the results of the serodiagnosis performed in Example 5.

As shown in FIG. 4, it is found that pulmonary adenocarcinoma can be detected in a high percentage of positive reaction and in a large antigen quantitiy by the serodiagnosis of the present invention. Positive results were observed in serum samples derived from pulmonary squamous cell carcinoma patients, pulmonary large cell carcinoma patients, gastric cancer patients, large intestinal cancer patients, pancreatic cancer patients, gallbladder or bile duct cancer patients, but the antigen quantity thereof was comparatively low. No positive results were obtained in serum samples from healthy subjects and pulmonary, gastric or pancreatic benign disease patients.

It is estimated from these results that the serodiagnosis of the present invention is useful in the clinical diagnosis of pulmonary adenocarcinoma.

While the invention has been described in detail and with reference to specific embodiments thereof, it will be apparent to one skilled in the art that various changes and modifications can be made therein without departing from the spirit and scope thereof.

What is claimed is:

1. An anti-human pulmonary adenocarcinoma monoclonal antibody ALC-864 secreted by a hybridoma having all of the identifying characteristics of hybridoma cell line ALC-864, accession no. FERM BP-1783, which belongs to the class IgG$_1$, and specifically binds to a protein antigen on human pulmonary adenocarcinoma cells but not to CEA or normal human lung cells as determined by enzyme-linked immunosorbent assay.

2. A hydridoma cell line having all of the identifying characteristics of hybridoma cell line ALC-864, deposited at the Fermentation Research Institute under the accession no. FERM BP-864.